United States Patent [19]

Genis

[11] 4,050,894
[45] Sept. 27, 1977

[54] STERILIZING AND STERILITY MAINTAINING APPARATUS FOR DENTAL AND SURGICAL TOOLS AND THE LIKE

[76] Inventor: Mariano Rodriguez Genis, 7a. Calle 3-37 Zona 1, Guatemala, Guatemala

[21] Appl. No.: 552,955

[22] Filed: Feb. 25, 1975

[51] Int. Cl.$^2$ .......................... A61L 3/00; A61L 3/02; B65D 81/24
[52] U.S. Cl. .......................................... 21/86; 21/99; 21/105; 206/363; 206/364; 206/365; 206/366; 206/367; 206/368; 206/369; 206/370
[58] Field of Search ........... 21/82 R, 82 H, 83, 85–87, 21/103, 105, 92, 93, 99, 100; 206/212, 306, 363–370; 427/443; 426/408, 301

[56] References Cited

U.S. PATENT DOCUMENTS

| 816,959 | 4/1906 | Briganti | 21/87 |
|---|---|---|---|
| 1,165,973 | 12/1915 | Howe | 206/306 |
| 1,187,498 | 6/1916 | Castle | 21/92 |
| 1,275,676 | 8/1918 | Halverson et al. | 21/93 |
| 1,508,799 | 9/1924 | Klett | 21/86 |
| 1,584,261 | 5/1926 | Vuolo | 21/105 UX |
| 1,699,001 | 1/1929 | Lauderdale | 21/86 |
| 2,318,380 | 5/1943 | Davis et al. | 21/2 |
| 2,417,626 | 3/1947 | Blocher | 21/82 H UX |
| 2,775,005 | 12/1956 | Weinberger | 21/82 R |
| 2,817,437 | 12/1957 | George et al. | 21/DIG. 4 |
| 3,511,169 | 5/1970 | Fritzberg et al. | 21/93 X |
| 3,681,008 | 8/1972 | Black | 21/93 |
| 3,779,707 | 12/1973 | Tabone | 21/83 X |

FOREIGN PATENT DOCUMENTS

| 783,300 | 4/1935 | France | 206/43 |
|---|---|---|---|
| 561,102 | 10/1932 | Germany | 21/85 |
| 87,679 | 10/1936 | Sweden | 21/87 |

Primary Examiner—Morris O. Wolk
Assistant Examiner—Bradley Garris
Attorney, Agent, or Firm—Owen, Wickersham & Erickson

[57] ABSTRACT

Sterilizing apparatus and method for dental and surgical tools. A main sterilizing chamber is provided with a cover having heating means and capsule-supporting means, which may comprise a plurality of removable trays, each one of which has a capsule-supporting basket. A plurality of tool-holding capsules are removably mounted in the capsule-supporting means and a normally solid petroleum product that is liquid at sterilizing temperatures surrounds and covers the capsules. The same kind of material is within each capsule in contact with the tool. The capsules are hermetically sealed by removable closures, and they include a tool-support structure inside. The tools are placed in the capsules and the capsules into the container, usually by means of the trays and basket, and then the sterilizer is heated for the necessary time at the necessary temperature to obtain sterilization, the heat acting through the medium of the normally solid petroleum product. After sterilization is completed, the baskets may be removed and drained, and the capsules may be stored. The petroleum product eventually solidifies and retains the product in sterile condition inside the sealed capsules.

6 Claims, 12 Drawing Figures

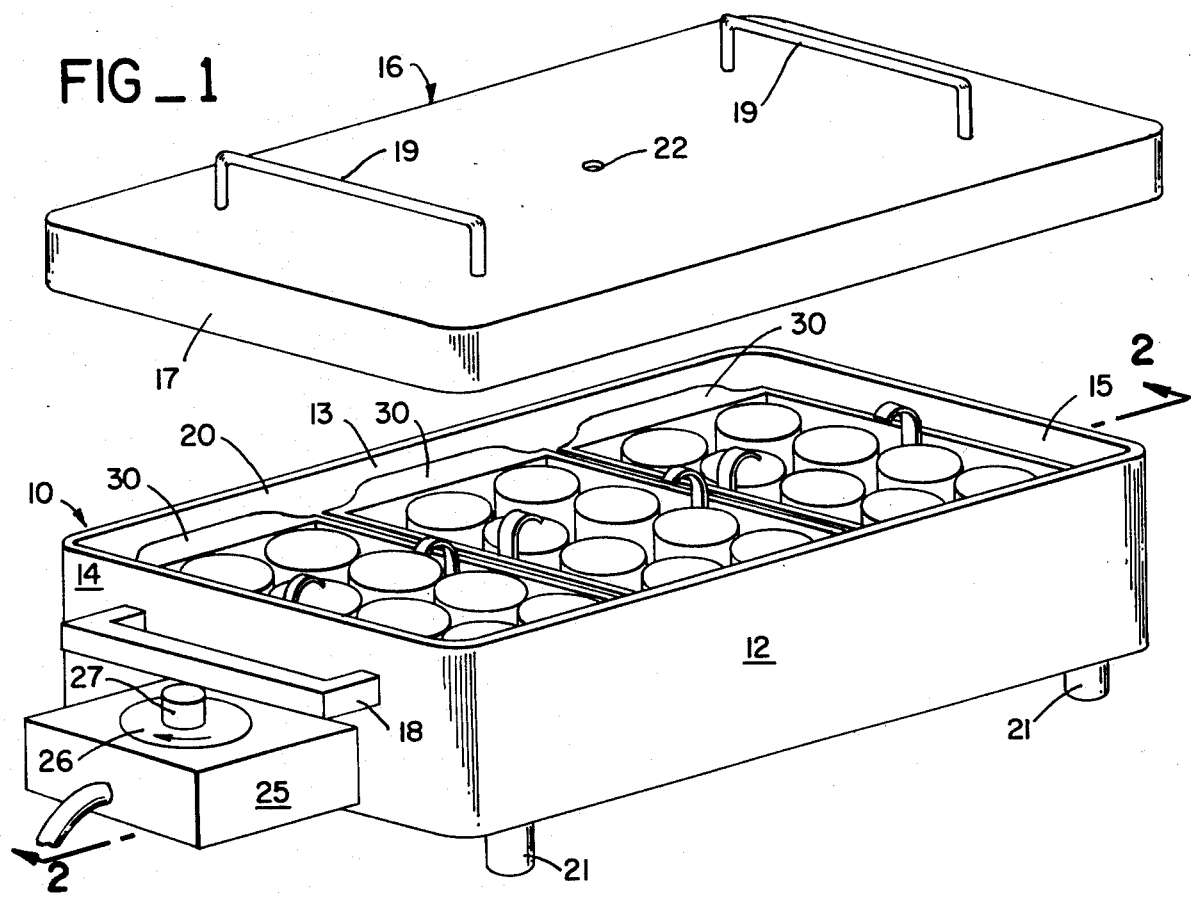
FIG_1
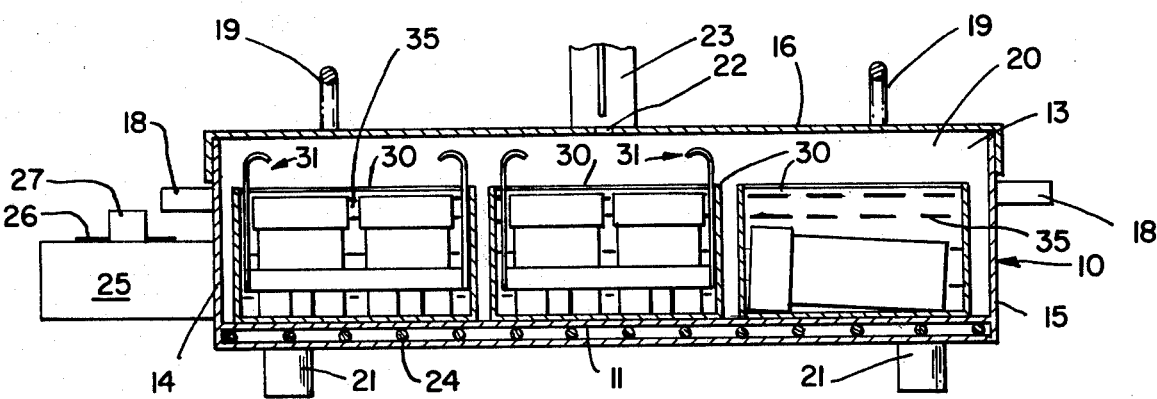
FIG_2
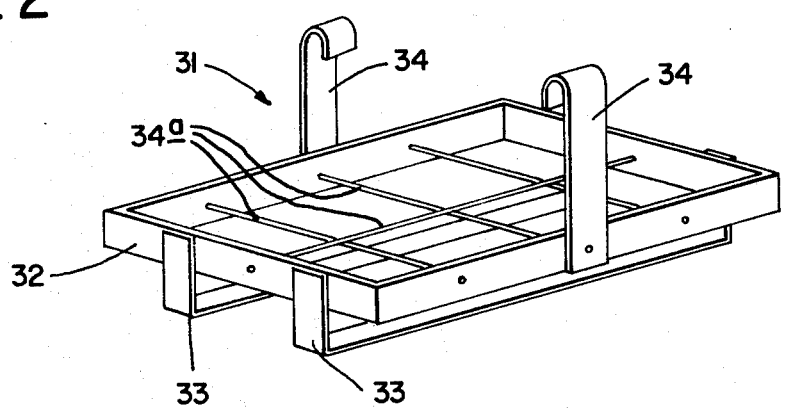
FIG_3

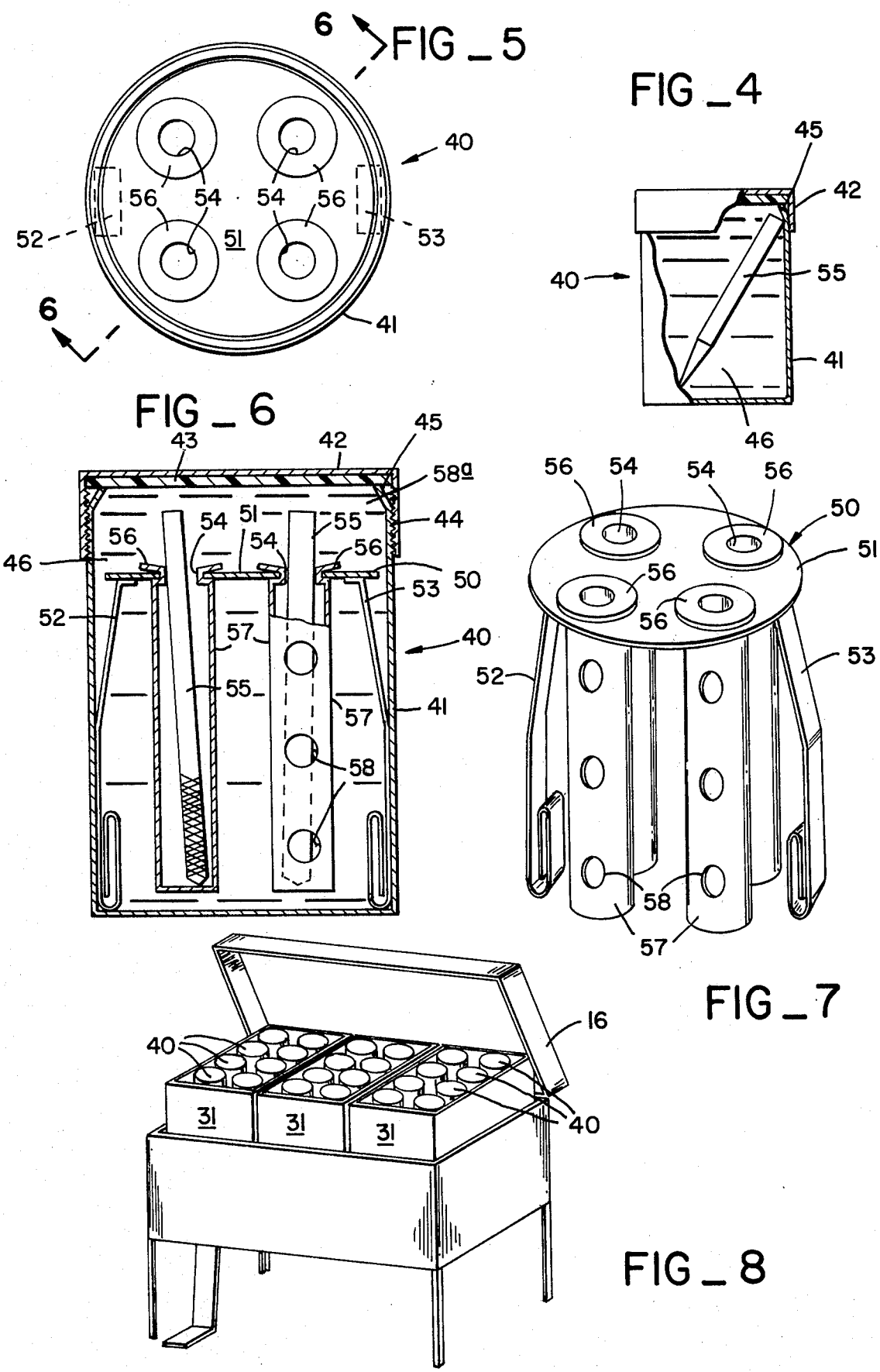

FIG_9
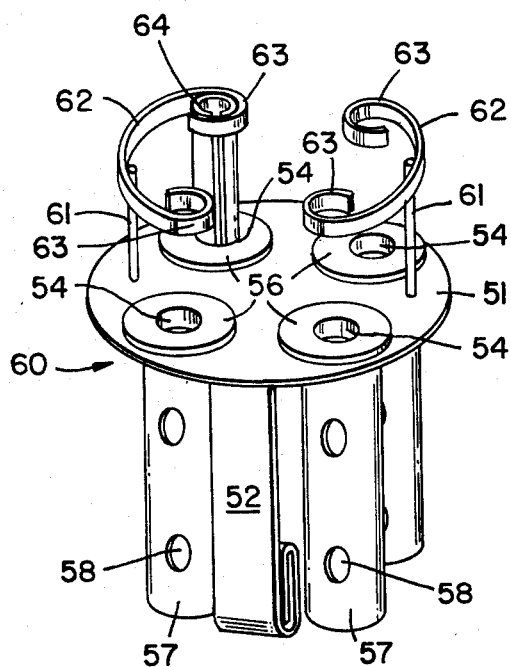
FIG_10
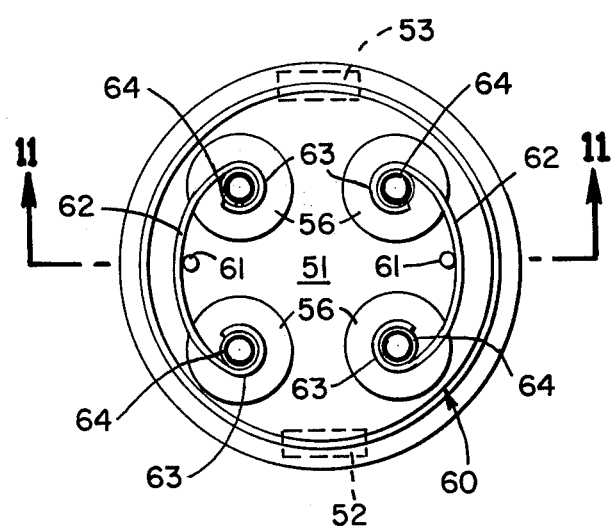
FIG_12
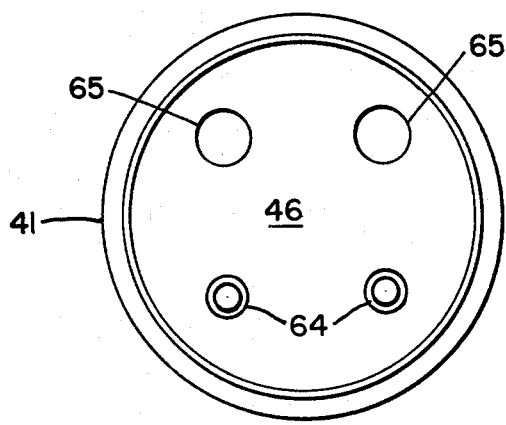
FIG_11
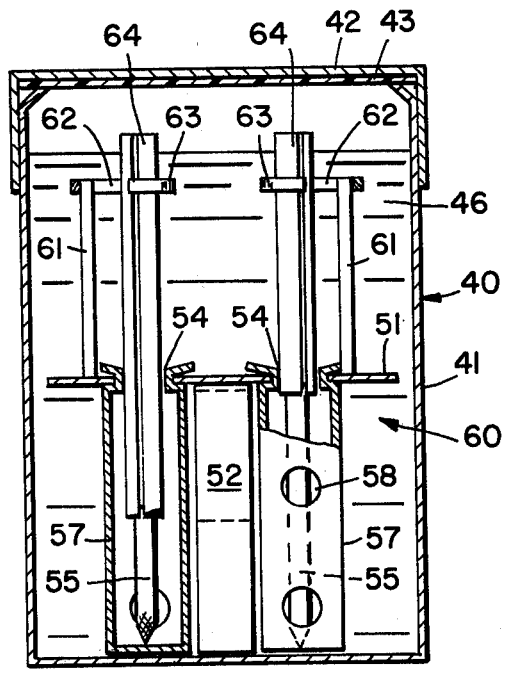

STERILIZING AND STERILITY MAINTAINING APPARATUS FOR DENTAL AND SURGICAL TOOLS AND THE LIKE

BACKGROUND OF THE INVENTION

This invention relates to improved method and apparatus for sterilizing dental and surgical tools and similar articles. It also includes novel capsules in which the sterilized tools are kept.

Various dental and surgical tools, such as drills, counterangles, and hand pieces, are sterilizable by the present invention. Previously, such tools have generally been sterilized in an autoclave and had either to be kept in such autoclave in order to remain in sterile condition or had to be in some way enclosed in hermetic containers. Moreover, autoclaves have tended to cause steel tools to rust, and the presence of oxidizing gas, chlorine, and so on have also affected the surface or edge of the instruments themselves, so as to reduce their effectiveness.

Thus, it is an object of the invention to provide improved apparatus and an improved method for sterilizing surgical drills, counterangles, hand pieces and the like.

It is also an object of the invention to keep the instruments that have been sterilized in the very medium by which they have been sterilized, so that one can have sufficient quantity in stock readily available to the surgeon for emergencies or scheduled operations.

Another object of the invention is to retain sterilized instruments in a classifiable type of capsule and to keep them completely decontaminated, doing so in any desired quantity.

A further object of the invention is to protect and maintain the sharpness of the drills and other cutting instruments by providing a sterilizing medium which is free from oxygen, air, chlorine, water, steam, and even nitrogen, as well as other substances that might affect the surface or edge of the instruments, both during sterilization and after sterilization has been completed and while the devices are in storage. As a result, it is possible to sterilize a number of instruments and to maintain a large stock of the instruments in quantities that may vary, depending upon the user.

SUMMARY OF THE INVENTION

The invention achieves the above objects by providing a main sterilizing container having a cover, suitable heating means, capsule-supporting means, and a plurality of tool-holding capsules that are removably mounted in the capsule-supporting means. The capsules have incorporated inside them a normally solid petroleum product, a hydrocarbon that is liquid at sterilizing temperatures, for surrounding the tools in the capsules. This petroleum product acts as a sterilizing medium during the sterilization operation and as a medium for retaining the tools in good condition after sterilization. The capsules are hermetically sealed by closures which can readily be removed. Moreover, during sterilization, spaces between the capsules themselves are filled with a normally solid petroleum product that is liquid at sterilizing temperatures, and this hydrocarbon product covers and surrounds the capsules.

The capsules themselves may include tool support means. An example of this is a disc with a hole for each of the tools to be supported and a depending perforate tube attached to the disc and extending down from around each such hole. Moreover, spring means or other retaining means are secured to the disc for holding the tool-support means relative to the walls of the capsule.

The apparatus may also include as the capsule-supporting means a plurality of removable trays that fit in the main container and carry a capsule-supporting basket. The trays have side walls that are higher than the capsules, so that the petroleum product can surround and cover the capsules, and the baskets enable removal of a group of capsules from the trays. The baskets themselves may have a perimetral rim, together with strips located below the rim and attached to the rim for supporting the capsules and also hook-like members extending up from the rim to facilitate withdrawal of the basket from the tray. There may also be a network of wire capsule-retention means supported by the rim above the supporting strips.

According to the method of the invention, the tools are each placed into a capsule containing a normally solid hydrocarbon product that is liquid at the sterilizing temperatures and then the capsules themselves are placed in a sterilizing chamber and surrounded by and covered with the same type of product. The sterilizing container is then heated to a suitable temperature and held there for a suitable time to obtain the necessary sterilization. Then the individual capsules are removed and stored without breaking their hermetic seal.

Other objects and advantages of the invention will become apparent from the detailed description which follows and from the drawings.

BRIEF DESCRIPTION OF THE DRAWINGS

In the drawings:

FIG. 1 is a partially exploded view in perspective of sterilizing apparatus embodying the principles of the invention.

FIG. 2 is a view taken in section along the line 2—2 in FIG. 1 with the cover in place.

FIG. 3 is a view in perspective of one of the capsule-supporting baskets.

FIG. 4 is a view in elevation with portions broken away and shown in section of one of the capsules with a tool therein.

FIG. 5 is a view on an enlarged scale of a capsule similar to that of FIG. 4 with the cover of the capsule removed.

FIG. 6 is a view in section taken along the line 6—6 in FIG. 5.

FIG. 7 is a view in perspective of the tool holder for the capsule of FIGS. 4 and 6.

FIG. 8 is a view in perspective of one of the baskets with a different type of capsule therein.

FIG. 9 is a view in perspective of a modified form of tool holder, with one of four removable tool guides in place.

FIG. 10 is a top plan view of an uncovered capsule with the tool holder of FIG. 9, four guides, and their tools in place.

FIG. 11 is a view in elevation and in section along the line 11 in FIG. 10 of a capsule including the tool holder of FIG. 9, with the cover in place, and the sterilizing medium solidified; and FIG. 12 is a top plan view of the opened capsule after sterilization and after removal of two of the tools and their guides.

DETAILED DESCRIPTION OF A PREFERRED EMBODIMENT

The sterilizing apparatus of this invention includes a main metallic container 10 having a horizontal bottom wall 11, generally vertical side walls 12 and 13, and generally vertical end walls 14 and 15. Although the container 10, as shown, is rectangular, it may be square or it may be cylindrical or any other suitable shape, though the preferable shape is rectangular and with rounded corners that facilitate cleaning. The container 10 also includes a lid 16 which has a depending rim 17 that keeps the container 10 closed securely during the sterilizing operation. The lid 16 as shown is flat, but it may be convex if desired. The container 10 preferably has a handle 18 at each end, and the lid 16 likewise preferably has a pair of handles 19, one located near each end. These may be made of suitable heat insulating material which is capable of withstanding sterilizing temperatures, so that it can be more easily handled.

The container 10, when closed, provides a sterilizing chamber 20 in which the sterilizing operation takes place. To prevent damage to the surface on which the sterilizing container rests, the container 10 may be provided with suitable legs 21. The container lid 16 preferably includes an opening 22 to receive a thermometer 23.

The dimensions of the container 10 may be varied according to the size of instruments to be accommodated or to the quantity of instruments to be processed in each sterilization operation and therefore may depend upon the number of instruments used by the clinic, hospital, or other place where the instruments are used. The container 10 may be made of heavy sheet metal, such as stainless steel, which is a preferable material, and the walls 11, 12, 13, 14, 15 may be either of single sheet thickness or may be of double sheet thickness, with space in between them to provide insulation. Insulation may be provided around the apparatus or between walls as desired, though it is not necessary to the practice of the invention.

The heat for sterilization may be produced by any desired means, including gas, but preferably it is done by electricity with the container 10 including a suitable heating element 24. For a small container 10 an element using 110 to 120 volts at 15 amps. is normally satisfactory. There may be an automatic thermostat 25 which may be secured to one end wall 14 of the container 10 and may be either fixed to that container wall 14 or removable therefrom. This thermostat 25 may have a dial 26 which is worked by hand with a suitable timer button 27 so that the operator can set the device at a certain temperature and then set the timer to determine the time of operation.

Many thermostats are available and a suitable type can be chosen from the shelf of a supplier. The type of thermostat used with electric frying pans is removable and can be removed after every use to prolong the life of the device. Also, it can be easily changed if the thermostat should become inoperative and the operator may keep replacements in stock. When the thermostat incorporates a timer, the automatic operation of shutting off is obtained. Thus, the thermostat may be set at any temperature between 150° to 350° F. and may operate to serve as a circuit breaker as well. The time of duration is preferably 20 minutes at 280° F. but other temperatures and times may be chosen as is known.

The mercury thermometer 23 may be installed in the opening 22 through the lid 16 during sterilization, so that the operator can determine that the proper sterilizing temperature is indeed being used, and the thermometer 23 may be left in during sterilization. Preferably the bulb at its bottom is suitably protected by a lining of perforate metal to avoid breakage of the mercury bulb. Suitable thermometers of this type are readily available.

The device may conveniently be provided with a series of removable trays 30, preferably made of stainless steel or aluminum, and these may vary in number and shape and dimension according to the size and capacity of the main container 10. They need not be used, but they are a convenience, each one of them providing a separate, compartment holding a number of capsules 40.

Each of the trays 30 is preferably provided with a suitable capsule-supporting basket 31. The basket 31 is made of a size to fit snugly within the tray 30 in order to avoid wasting room. The basket 31 may have a perimetral rim 32, such as the rectangular rim 32 shown; secured to the rim 32 may be a pair of flat U-shaped strips 33 which extend down and then pass horizontally across between opposite edges of the rim 32 to support the capsules 40. Additionally, wires 34a may be secured to the rim 32 and extend horizontally across it to provide a stabilizing system for supporting the capsules 40. The baskets 31 may also be provided with a pair of upwardly extending hooklike members 34 secured to the rim 32 to enable withdrawal of the basket 31 with the aid of a pair of tongs or other suitable apparatus. Instead of hook-like members 34, other suitable apparatus may be used. The purpose of the basket 31 is to facilitate the removal of a plurality of capsules 40 from a bed of hot sterilizing material 35 in which they will be immersed and to enable draining the liquefied material 35 back into the tray 30 and then placing the capsules 40 on an adequate surface to enable the capsules 40 to cool and to enable at the same time the insertion of other baskets 31 with other capsules 40 to be sterilized. This makes it possible to sterilize great numbers of instruments in the same sterilizing material 35 and thereby saves on time as well as on the electricity or gas or other source of heat.

In between the capsules 40 in each tray 30 (when the trays 30 are used or in the main container 10 when the trays 30 are not used) is the bed of suitable sterilizing medium 35. This medium 35 is preferably a hydrocarbon petroleum material which is solid at ordinary temperatures but is a liquid at the sterilizing temperatures. An example of a material which is very satisfactory is solid petrolatum or white petroleum jelly. This material is pure and clean, being a mixture of hydrocarbons. It contains no oxygen or chlorine or air. This material is a good lubricant as well as a good medium for sterilization. The medium 35 is liquefied before the baskets 31 are set in place, and thereby any included or occluded air and gases are driven out of the medium 35, and then it is kept up to a level in the trays 30 higher than the top of the capsules 40 themselves, since the tray walls are taller than the capsules. Thus, the capsules 40 are not only surrounded but are covered by this hot liquefied petroleum jelly 35. If things are kept clean, the same bath of petroleum jelly may be used over and over with replenishment and addition from time to time.

It is possible to use larger sterilizers with treadle-operated lids, so that one can place his foot on the treadle to open and close the lid, and this may be also made for simultaneously lifting the baskets 31 containing the capsules 40 and holding them at a convenient height to let the liquefied sterilizing petroleum jelly drain from them and to let the temperature drop for awhile, so that the baskets 31 can be conveniently handled by suitable apparatus and moved to the top of a suitable counter. Then baskets 31 with new capsules 40 may be inserted and by reversing the treadle operation, the baskets 31 may be automatically lowered and inserted in the sterilizing substance and the lid 16 closed.

An important part of the invention is the use of the capsules 40. These may be of a size suitable for the tools which they are to contain and may therefore vary in size, depending on the tools. Preferably, they are made of stainless steel or aluminum. They may be cylindrical tubes 41 with a threaded lid 42 provided with a suitable washer or inner lining 43 of pasteboard or asbestos or gasketing material sufficient to provide an airtight closure, because it is important for these devices to be hermetically sealed so that they can retain the sterilization. The capsules 40 may have lids at both ends for some tools, but that is not usually essential. The thickness of the walls 41 of the capsule is adequate to their size, and the thread 44 is preferably a relatively short one with just sufficient threading to assure adequate locking. The edge 45 of the tubes where the lid goes may be bent slightly inwards to enable a perfectly sealed enclosure to make sure that the essential hermetic closure is obtained. As indicated, the size of the capsules 40 depends upon the number and size of the objects they are to contain. Small capsules 40 may be used for a single counter-angle drill and larger capsules 40 may be used for three or four of the same type of drill. Longer capsules 40 may be used for hand piece drills and still longer ones for other surgical drills. The capsules 40 are made large enough for sterilizing counter angles and hand pieces in some instances, with these preferably being lidded at both ends to enable the removal of the instruments that are being sterilized.

Once again, a sterilizing medium 46 which is derived from petroleum and which is liquid at sterilizing temperatures but solid at ordinary temperatures is preferably employed. The hydrocarbon material employed may be again white petroleum jelly or petrolatum or it may be a mixture of petrolatum with paraffin in equal parts or in other proportions. For drills, I have found that a mix of equal proportions of white petroleum jelly and paraffin is quite suitable. For counter angles and hand pieces, I recommend the use of pure white petroleum jelly or suitable mineral petroleum derived products having the characteristics already described.

Inside the capsules 40 there may not need to be any particular holder for the tool, depending on the type of tool, but in many instances it is preferable to have such a tool holder 50 to hold the tool in its proper orientation or to hold a plurality of tools and keep them separated from each other. The tool holder 50 may be made in various manners, but the presently preferred form comprises a disc 51 which fits with adequate clearance into the cylindrical capsule portion 41 and to which are secured a pair of outwardly extending spring clips 52 and 53 which are forced radially inwardly during insertion of the tool holder 50 into the capsule body 41 and help to retain the tool holder 50 in any desired height within the capsule 40. Each disc 51 is perforated by the number of holes 54 corresponding to the number of tools 55 to be installed, ranging from one upwardly, of course. Depending from each hole and preferably supported by a flange 56 engaging the disc 51 and otherwise supported in some manner by the disc are tubes 57, one tube for each hole. The tubes 57 are perforated by openings 58 and give free access to the liquid sterilizing medium 46. They also are adequate to retain the tools 55 being sized properly. Preferably, the drills 55 protrude about one-fourth of their length at the top of the tubes 57 into a space 58a above the disc 51 and below the cap 42. The tool holders 50 may have a small ring in the middle to facilitate their removal from the capsule 40 for cleaning and changing the sterilizing substance 46. The instrument holders 50 may be constructed of a suitable metal sheet of suitable metal such as stainless steel or aluminum, the perforations 58 enabling the sterilizing substance 46 to circulate freely within the tubes 57. The tool holders 50 with their tools 55 may be inserted in the capsule 40 before adding the petroleum jelly or other suitable material, or the petroleum jelly may be in place and then the tool holders 50 inserted into it when it is liquid.

In operation, the petroleum jelly 46 may be liquefied, if desired, or the tools 55 may be inserted into a capsule 40 either before adding the petroleum jelly in liquid form or while it is still in a viscous solid form. In any event, the tools 55 may be inserted into the capsules 40 and the capsules 40 placed in baskets 31 and the baskets 31 inserted into the trays 30, once the petroleum jelly 35 there has become liquefied in the trays 30. After sterilization, the baskets 31 of capsules 40 are removed, the liquid petroleum product 35 is drained back into the trays 30, and then the capsules 40 are set aside to cool. The sterilized capsules 40, if properly closed and preferably with their exterior cleaned from any remaining petroleum jelly, that is, the sterilizing substance 35 from the tray 30, may be placed in individual cardboard boxes of proper size, and the boxes may be sealed and strapped to maintain the capsules 40 in proper condition and may be labeled to indicate the number and type of the instruments 55 contained in each capsule 40. The capsules 40 may in this manner be shipped and stored until it is time for using them.

FIGS. 9-12 show the use of a modified form of tool holder 60, the disc 51 of which and the portions therebelow are identical with those of the tool holder 50 and are so numbered, as are the flanges 56. In addition, however, there are two upstanding posts 61 secured to the disc 51. At their upper ends, the posts 61 each have a shaped metallic wire or strip 62, each extending out and defining two rings 63 directly overlying the openings 54. Also, each tool 55 is carried by a tool guide 64 that is much taller than the tool. The guide 64 is shown here as a split tubular member, open along the split, preferably made from a thin sheet of aluminum. The guides 64 (1) make it easier to find the tools 55 after the sterilizing medium 46 has hardened (the tools 55 are especially difficult to find if they are short and there are no guides), (2) enable the total immersion of each tool 55 in the sterilizing medium 46 during and after sterilization, with the top of the medium 46 lying at least about 1 centimeter above the tool's upper end (this is important in maintaining the sterility of the tools for a long, even indefinite, period of time), and (3) enable reinsertion (when the tool 55 and its guide 64 have been taken out, the hardened sterilizing medium 46 presents a visible hole 65 that facilitates reinsertion of the tool 55 and its guide 64 for resterilization). Without the structure of the tool holder 60 and the guides 64, some tools 55 tend to be elevated during sterilization and to rise out of the tubes 57. Then they become difficult to find in the hardened sterilizing medium 46.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

I claim:

1. Sterilizing and sterility-maintaining apparatus for dental and surgical tools and the like, including in combination a main sterilizing container having a cover, heating means, and capsule-supporting means, a plurality of imperforate tool-holding capsules removably mounted in capsule-supporting means, said capsules having removably and hermetically sealable closures, and a normally solid petroleum product that is liquid at sterilizing temperatures, retained in each said capsule and surrounding and covering at least the operative portions of the tools in said capsules and serving in solidified state to aid in retaining the sterility of each said tool after completion of the sterilization and after said capsule is opened, at least one of said capsules including tool support means therewithin, each said tool support means comprising a disc covered by said petroleum product and having a perforation therethrough for each tool to be supported, a perforate tube for housing each said tool, attached to said disc below each said perforation through said disc, retention means secured to said disc for holding said disc relative to said capsule, and upstanding post means secured to said disc and having support means extending out therefrom for supporting the upper end of a said tool and defining a support ring-like structure overlying each said perforation.

2. The sterilizing and sterility-maintaining apparatus of claim 1 wherein each said tool support means also includes a perforate tool guide for encasing a portion of each said tool and extending above the upper end of said tool, each said tool guide resting in a said perforate tube and being aligned vertically by a said ring-like structure.

3. Sterilizing and sterility-maintaining apparatus for dental and surgical tools and the like, including in combination a main metal container having a bottom wall and side walls, a cover for said main container, means for heating said main container to sterilizing temperatures, a plurality of removable trays in said container normally but removably resting on said bottom wall and having a tray bottom and tray sides, a capsule-supporting basket removably mounted in each said tray, a plurality of imperforate capsules removably mounted in each said basket, said capsules having removably and hermetically sealable closures and being shorter than said tray sides, tool support means in said capsules for supporting the tools to be sterilized, and a normally solid petroleum product that is liquid at sterilizing temperatures retained in said capsules and surrounding and covering at least the operative portions of the tools in said capsules and serving when solidified to aid in retaining the sterility of each said tool after completion of sterilization and after said capsule is opened each said tool support means comprising a disc covered by said petroleum product having an opening therethrough for each tool to be supported, a perforate tube for housing each said tool, located below each said opening and supported by said disc, spring means secured to said disc for engaging the walls of said capsule and retaining the disc at a desired position in said capsule, and upstanding post means secured to said disc and having support means extending out therefrom for supporting the upper end of a said tool and defining a support ring-like structure overlying each said opening.

4. The sterilizing and sterility-maintaining apparatus of claim 3 wherein each said tool support means also includes a perforate tool guide for encasing a portion of each said tool and extending above the upper end of its said tool, each said tool guide resting in a said perforate tube and being aligned vertically by a said ring-like structure.

5. A holder for dental and surgical tools and the like, in which the tools may be sterilized and retained in sterile condition, including in combination an imperforate capsule having a removably and hermetically sealable closure, and tool support means in said capsule for supporting each tool in said capsule, said tool support means comprising a perforate disc having a hole for each tool to be supported thereby, a depending perforate cylinder beneath each said hole for each tool to be supported thereby depending from said disc, spring retention means depending from said disc for engaging the walls of said capsule, and an upstanding post means secured to said disc and having support means extending out therefrom and defining a support ring-like structure overlying each said hole to enable locating and retrieving each supported tool.

6. The holder of claim 5 including a tool guide for encasing a portion of each said tool and extending above the upper end of said tool, said tool guide resting in a said cylinder and being aligned vertically by a said ring-like structure.

* * * * *